US006478881B2

(12) United States Patent
Ellis et al.

(10) Patent No.: US 6,478,881 B2
(45) Date of Patent: Nov. 12, 2002

(54) CONTACT LENS CLEANING SOLUTION

(75) Inventors: Jeanne Y. Ellis, Lynnfield, MA (US); Edward J. Ellis, Lynnfield, MA (US)

(73) Assignee: Vista Scientific L.L.C., Andover, MA (US)

( * ) Notice: Subject to any disclaimer, the term of this patent is extended or adjusted under 35 U.S.C. 154(b) by 0 days.

(21) Appl. No.: 09/795,766

(22) Filed: Feb. 28, 2001

(65) Prior Publication Data

US 2001/0020000 A1 Sep. 6, 2001

Related U.S. Application Data

(63) Continuation of application No. 09/352,010, filed on Jul. 12, 1999, now abandoned.

(60) Provisional application No. 60/133,837, filed on May 12, 1999.

(51) Int. Cl.[7] .............................. A61L 2/18; C11D 3/48

(52) U.S. Cl. ............................ 134/42; 134/39; 134/40; 514/840; 510/112; 510/384; 510/434; 510/435; 510/471; 510/477; 510/533; 510/163; 510/400; 510/420; 510/421; 510/433; 510/475

(58) Field of Search ................................ 510/112, 384, 510/434, 435, 471, 477, 533, 163, 400, 420, 421, 433, 475; 134/39, 40, 42; 514/840

(56) References Cited

U.S. PATENT DOCUMENTS

| | | | | | |
|---|---|---|---|---|---|
| 4,836,986 | A | * | 6/1989 | Ogunbiyi et al. | 422/28 |
| 5,858,937 | A | * | 1/1999 | Richard et al. | 510/112 |
| 5,965,088 | A | * | 10/1999 | Lever et al. | 422/28 |
| 6,143,244 | A | * | 11/2000 | Xia et al. | 422/28 |
| 6,153,568 | A | * | 11/2000 | McCanna et al. | 510/112 |
| 6,309,596 | B1 | * | 10/2001 | Xia et al. | 422/28 |
| 6,309,658 | B1 | * | 10/2001 | Xia et al. | 424/405 |

* cited by examiner

*Primary Examiner*—Yogendra N. Gupta
*Assistant Examiner*—Brian P. Mruk
(74) *Attorney, Agent, or Firm*—Cantor Colburn LLP

(57) ABSTRACT

The present invention is based on the unexpected finding that the combination of a carboxylate containing anionic polymer, of molecular weight greater than about 1000 daltons, with cleaning agents, provides improved contact lens cleaning preparations. The present invention includes contacting a soiled contact lens with an aqueous solution comprising an anionically charged polymer and a surfactant or surfactant combination selected from the classes of nonionic surfactants, anionic surfactants, and amphoteric surfactants.

12 Claims, No Drawings

CONTACT LENS CLEANING SOLUTION

CROSS REFERENCE TO RELATED APPLICATIONS

This application is a continuation of U.S. patent application Ser. No. 09/352,010, filed Jul. 12, 1999, (now abandoned) which claims the benefit of U.S. Provisional patent application 60/133,837, filed May 12, 1999, both of which are hereby incorporated by reference in their entirety.

FIELD OF THE INVENTION

The present invention relates to a composition for use in the care of contact lenses, and the like, and more particularly, relates to a cleaning solution for use with contact lenses.

BACKGROUND OF THE INVENTION

Contact lenses are subjected to the ocular environment for long periods of time each day. As a result of being in contact with the tear film and ocular debris, lenses have a tendency to build up surface deposits. The deposit may be formed from endogenous materials, such as proteins, lipids and mucins, but also may be the result of exogenous materials, such as cosmetic ingredients. To ensure comfortable wear and good vision, these surface deposits must be removed periodically, usually once a day for rigid gas permeable lenses and daily wear soft hydrogel lenses. For flexible wear lenses the cleaning may be less frequent.

Contact lens cleaners can be classified into two categories, primary, or "daily cleaners" and secondary, or "adjunct" cleaners. The daily cleaners are surfactant based and are formulated to target the soils most commonly found on either soft hydrogel lenses or rigid lenses. The adjunct cleaners are generally enzyme based and target proteinaceous matter. These enzyme cleaners are usually recommended for weekly use with soft hydrogel lenses. However, more recently, enzyme treatment of rigid lenses has been gaining favor.

The contact lens cleaners on the market today contain a surfactant and/or combination of surfactants, selected from the non-ionic, anionic or amphoteric categories. The use of a cationic surfactant in a contact lens cleaner is rare. Abrasives, or particulate matter in contact lens cleaners has been taught to assist the surfactant(s) in removal of soils. There have been reports in the contact lens industry that cleaners with harsh abrasives will change the power of rigid lenses over time due to a "polishing" effect.

The cleaning process for contact lenses can be either active, digital rubbing of the lens surface, or passive, soaking the lens in the cleaning solution. These cleaning processes may be combined, that is, the contact lens is removed from the eye, digitally rubbed with the cleaning solution, then placed in that same cleaning solution overnight to allow passive cleaning to occur. Examples of this regimen for rigid lens would be the Boston Simplicity® solution and the Menicon Claris® system. For soft hydrogel lenses there are a number of products available that are considered multipurpose solutions, that is, cleaning, soaking and disinfection. Examples include Bausch & Lomb Renu®, Alcon Optifree®, Ciba Solocare® and Allergan Complete®.

The surfactant(s) in contact lens cleaners serves a dual role. One role is to "solubilize" the soil on the lens into micelles. The other role is to "displace" the soil from the lens surface. This is accomplished by breaking the hydrophobic interaction between the soil and the lens surface, leading to a more thermodynamically preferred state. The use of abrasives help "displace" soils from the surface, thus aiding the surfactant(s).

Surfactant based contact lens cleaners on the market today vary in performance depending on the surfactant system chosen and the regiment recommended. For instance, surfactant/abrasive cleaners that are rinsed from the lens perform reasonably well, while multipurpose solution cleaners tend to be less effective due to the requirement that the cleaner be non irritating to the eye. Because soft hydrogel lenses have a rather porous structure, surfactants will tend to be absorbed into the lens structure, only to be released later into the ocular environment during lens wear.

Given the many types of contact lenses available today, i.e. low to high oxygen permeable rigid lenses, conventional and disposable hydrogel lens various water contents and surface charges, and the new soft silicone hydrogel lenses, there is a need for improved cleaning products and processes. The trend is toward more efficacious and convenient cleaning products that provide a margin of safety when used by the patient.

SUMMARY OF THE INVENTION

The present invention is based on the unexpected finding that the combination of a carboxylate containing anionic polymer, of molecular weight greater than about 1000 daltons, with cleaning agents, provides improved contact lens cleaning preparations. The cleaning process of the present invention includes contacting a soiled contact lens with an aqueous solution comprising an anionically charged polymer and a surfactant or surfactant combination selected from the classes of nonionic surfactants, anionic surfactants, and amphoteric surfactants.

The combination of anionic polymer with surfactant(s) may further comprise buffers and an antimicrobial compound. The subject preparations may be in the form of a stand alone cleaner to be used in combination with a wetting, soaking and disinfection solution. Alternatively, the subject preparations may be in the form of a one step cleaner that provides simultaneous disinfection and cleaning of contact lenses. In preferred embodiments of the present invention the subject preparations are utilized as cleaning solutions for rigid gas permeable lenses. Furthermore, in preferred embodiments the subject compositions also provide a one step cleaning regimen which utilizes only one solution for both cleaning and disinfecting soft hydrogel contact lenses. As such, the present invention offers distinct and significant advantages over known cleaning regimens for contact lenses.

DETAILED DESCRIPTION OF THE PREFERRED EMBODIMENT:

It is an object of this invention to provide improved cleaning preparations for contact lenses. This is accomplished by agents incorporated into the cleaning preparations that prevent redeposition of removed soils during the cleaning process. The contact lens cleaning art has not yet recognized that soil removal from the contact lens is an equilibrium process in which removed soils can redeposit on the lens surface:

Deposited - - - > Removed

Soils < - - - Soils

This phenomenon has been recognized in the unrelated art of laundry cleaning products. As a result of investigating this phenomenon, certain compounds have been found useful in preventing redeposition of removed soils. These compounds are commonly referred to as "antisoils" or "antiredeposition agents". These agents are generally polymeric and contain an abundance of negative charge at a pH of 7. The use of certain antiredeposition agents in contact lens cleaning preparations has been found to be advantageous. While not being limited by any particular theory, it is believed that the incorporation of an antiredeposition agent into a contact lens cleaning solution provides several distinct advantages.

In accordance with the present invention, excellent cleaning results are obtained on soiled contact lens, particularly rigid gas permeable lenses. The lenses are cleaned quickly and thoroughly and the present cleaning solution rinses easily and completely from the lens surface. This negates the need for high levels of surfactant and/or abrasives often present in commercially available contact lens cleaning solutions. A particularly useful class of antiredeposition agents are polyanionic components containing multiple carboxylate groups. Preferred carboxylate containing polyanionic components include: metal carboxymethyl celluloses, metal carboxymethyl hydroxyethyl celluloses, metal carboxymethyl starches, metal carboxymethyl hydroxyethyl starches, metal polyacrylates and polymethacrylates, and metal salts of copolymers containing acrylic and methacrylic acid.

The present polyanionic components often can exist in the un-ionized state, for example, in the solid state, in combination with a companion or counter ion, in particular a plurality of discrete cations equal in number to the number of discrete anionic charges so that the un-ionized polyanionic component is electrically neutral. For example, the present un-ionized polyanionic components may be present in the acid form and/or in combination with one or more metals. Since the polyanionic components are preferably ophthalmically acceptable, it is preferred that the metal associated with the un-ionized polyanionic component be ophthalmically acceptable in the concentrations used. Particularly useful metals include the alkali metals, the alkaline earth metals, for example calcium and magnesium, and mixtures thereof. Sodium and potassium are very useful to provide the counter ion in the un-ionized polyanionic component. Polyanionic components which, in the un-ionized states, are combined with cations other than $H^+$ and metal cations can be employed in the present invention.

In the practice of this invention, the most preferred polyanionic components are selected from anionic cellulose derivatives, anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like an admixtures thereof), anionic polymers derived from the copolymerization of acrylic acid with maleic acid. It should be understood that more than one anionic polymer may be employed in a preparation when practicing this invention.

The molecular weight of the anionic polymers described in this invention can range from about one thousand daltons to several hundred thousand daltons. For the anionic acrylic polymers the preferred molecular weight ranges from about 1000 daltons to about 100,000 daltons. When anionic cellulose derivatives are employed the preferred molecular weight range is from about 70,000 daltons to about 700,000 daltons.

The cleaning preparations described therein are preferably aqueous based and contain at least about 0.01 percent by weight of the anionic polymer of mixtures of anionic polymers. In one exemplary embodiment, the water soluble polymer is present in an amount from about 0.01 to about 10% by weight of the total composition.

The subject aqueous cleaning solutions may also contain various other components including, but not limited to, buffering agents, tonicity adjusting agents, chelating and/or sequestering agents, viscosifiers, surfactants, humectants, and antimicrobial agents. Furthermore, the subject solutions preferably have a pH between about 6.0 and about 8.0.

Any pharmaceutically acceptable buffer system may be utilized in the present invention and include phosphates, borates, acetates and carbonates. Most preferred are the phosphate and borates at total levels of from about 0.1% by weight to about 1.5% by weight of the total composition.

Tonicity adjusting agents refer to those agents that are used to modify the osmolality of an ophthalmic formulation. Examples of useful tonicity agents include, but are not limited to, sodium chloride, potassium chloride, mannitol, sorbitol, glycerin, propylene glycol and mixtures thereof. In one embodiment the tonicity agent is selected from inorganic salts and mixtures thereof.

The viscosity of the cleaning compositions may be adjusted by varying the concentration of the carboxylate containing anionic polymers described in the present invention. In practice, cleaning compositions for soft hydrogel contact lenses are generally in the viscosity range of about 1 cps (mPa.s) to about 50 cps (mPa.s). Cleaning compositions for rigid contact lenses generally are more viscous than those for soft hydrogel lenses and range in viscosity from about 10 cps (mPa.s) to about 400 cps (mPa.s). When higher consistency cleaning formulations are desired, viscosity builders may be employed. Examples of useful viscosity builders include, but are not limited to, hydroxyethylcellulose, hydroxypropylmethylcellulose, polyvinylpyrrolidone, polyvinylalcohol and mixtures thereof.

Suitable surfactants are utilized in the practice of this invention and can be either cationic, anionic, amphoteric or non-ionic. Examples of suitable surfactants include, but are not limited to:

Cationic Surfactants:

Alkylamidopropyl phosphatidyl PG-dimonium chloride

Alkyl phosphatidyl PG-dimonium chloride

Polyoxyethylene dihydroxypropyl alkylamonium chloride

The cationic surfactants may be employed alone or in admixtures thereof.

Anionic Surfactants:

Sodium alkylbenzene sulfonates

Sodium alkyl sulfates

Sodium α-olefin sulfonates

Sodium polyoxyethylene alkylether sulfates

Sodium alkyloylmethyltaurinate

Sodium alkyloylsarcosinate

Sodium polyoxyethylene alkylether phosphates

Sodium di(polyoxyethylene alkylether)phosphates

Sodium polyoxyethylene alkylphenylether sulfates

The anionic surfactants may be employed alone or in admixtures thereof.

Amphoteric Surfactants:

Alkoamphoglycinates

Alkoamphocarboxyglycinates

Alkoamphopropionates

Alkoamphocarboxyproprionates

Alkoamphopropylsulfonates

Alkylbetaines

Dihydroxyethylalkylglycinates

Alkylamidopropylbetaines

Alkylamidopropylhydroxysultaines

Alkylaminoproprionates

Alkylaminodiproprionates

Alkylaminoacetate

Alkylaminodiacetates

The amphoteric surfactants may be employed alone or in admixtures thereof.

Non-ionic Surfactants:

Polyoxyethylene higher fatty acid esters

Higher fatty acid esters with polyoxyalkylene-polyoxyethylene copolymers

Higher fatty acid esters with polyhydric alcohols

Higher fatty acid esters with polyoxyethylene polyhydric alcohols such as polyoxyethylene glyceryl fatty acid esters and polyoxyethylene sorbitan fatty acid esters Polyglycerin fatty acid esters Polyoxyethylene alkyl ethers Polyglycerin ethers with alcohols Polyoxyethylene fatty acid amides Polyoxyethylene alkylamines Polyoxyethylene alkylphenyl ethers Condensate of polyoxyethylene alkylphenol ether with formaldehyde Polyoxyethylene-polyoxypropylene block copolymers Polyethyleneglycol adduct of hydrogenated castor oil Castor oil or sterol Polyoxyethylene sorbitan fatty acid esters The non-ionic surface active agents may be employed alone or in admixtures thereof.

The preparations of the present invention preferably include at least one antimicrobial agent. The antimicrobial agents commonly used in ophthalmic preparations are quaternary ammonium salts. The presence of an anionic polymer will greatly reduce the effectiveness of cationic antimicrobial agents due to molecular binding. For this reason antimicrobials that do not interact with anionic polymers are preferred in the practice of this invention.

Such antimicrobial agents are:

Methyl paraben

Ethyl paraben

Propyl paraben

Butyl paraben

Sorbic acid (or the salt form)

2-bromo-2-nitropropane-1,3-diol, dichlorobenzyl alcohol 2-phenoxyethanol

Dimethylol dimethylhydantoin

Diazolidinyl urea

The antimicrobial agents utilized in this invention may be used alone or in admixtures thereof. The amount of antimicrobial agent or agents used will depend on the chemical structure of the antimicrobial agent as well as the chemical nature of the other ingredients included in the cleaning preparation. Typically, such agents or combination of agents are present in concentrations from about 0.001% by weight to about 0.5% by weight, and more preferably from about 0.05% by weight to about 0.5% by weight.

Examples of preferred antimicrobial chelating agents include ethylene-diamine-tetraacetic acid (EDTA), and its salts, which are normally employed in amounts from about 0.01% by weight to about 0.5% by weight. Other known chelating (or sequestering agents) such as sodium citrate and nitrilo-triacetic acid can also be used.

Contact lenses are cleaned by contacting the lens with the cleaning preparations of the present invention. Preferably the cleaning preparation is in the form of a homogeneous, aqueous based solution. Cleaning may be accomplished by simply soaking a lens in the cleaning solution. Alternatively, the cleaning may be achieved by placing a few drops of the cleaning solution on each surface of the lens and then digitally rubbing the lens for a few seconds. A combination procedure involving both digital rubbing and soaking in the cleaning solution may also be employed.

In some cases, particularly when antimicrobial agents are present in the cleaning formulation, the aqueous solution of this invention not only cleans the lens, but also disinfects.

As an illustration of the present invention, several examples are provided below. These examples serve only to further illustrate aspects of this invention and should not be construed as limiting the invention.

EXAMPLES

Examples 1 through six 6 the utility of a number of anti-soil redeposition agents in various contact lens cleaning formulations. The Examples also teach the compatibility of these anti-soil redeposition with a wide variety of surfactants. A key to the surfactants used in Example 1 through 6 is given in Table I.

TABLE I

| Class | Surfactant | Trade Name | % Active | Supplier |
|---|---|---|---|---|
| Anionic | ammonium salt of sulfated nonyl-phenol ethoxylate | Alipal E115 | 30% | Rhone-Poulenc |
| | ammonium lauryl sulfosuccinate | Monamate LNT-40 | 40% | Mona |
| | sodium trideceth sulfate | Rudapex EST-30 | 30% | Rhone-Poulenc |
| Amphoteric | Lauroauphoacetate | Monateric LM-M30 | 36% | Mona |
| | cocamidopropyl betaine | Monateric CAB-LC | 35% | Mona |
| | sodium dicarboxy-ethyl phosphoethyl imidazoline | Phosphoteric TC-6 | 35% | Mona |
| Nonionic | Octylphenoxy-polyethoxy ethanol | Triton X-100 | 100% | Union Carbide |
| | poloxyethylene sorbitan alkyl ester | TWEEN 20 | 100% | FCI Americas |
| | block copolymer of ethylene oxide and propylene oxide | Pluronic F-127 | 100% | BASF |

The formulations presented in Examples 1 through 6 are prepared by dissolving all the ingredients in the deionized water, with no particular order required. After the ingredients have completely dissolved, the formulation is stirred for at least two hours before the physical properties are measured.

EXAMPLE 1

The following rigid contact lens cleaning formulations (in weight %) illustrate the use of a polyacrylic acid, sodium salt, MW 1200, as the anti soil redeposition agent.

| | A | B | C |
|---|---|---|---|
| Alipal E115 | 0.5 | 1.0 | 2.0 |
| Tween 20 | 0.5 | 1.0 | 2.0 |
| Polyacrylic acid sodium salt (45%) | 5.0 | 6.0 | 10.0 |
| Hydroxyethyl cellulose* | 0.6 | 0.6 | 0.6 |
| Sodium borate | 0.1 | 0.1 | 0.1 |
| Boric acid | 0.2 | 0.2 | 0.2 |
| Methyl paraben | 0.15 | 0.15 | 0.15 |
| EDTA | 0.05 | 0.05 | 0.05 |
| Deionized water (qs to) | 100 | 100 | 100 |
| *Natrosol 250MP | | | |
| pH | 8.0 | 8.0 | 8.0 |
| Viscosity (cps) | 162 | 175 | 221 |
| Appearance | clear | clear | clear |

EXAMPLE 2

The following rigid contact lens cleaning formulations (in weight %) illustrate the use of a polyacrylic acid, sodium salt, MW 30,000, as the anti soil redeposition agent.

| | A | B | C | D |
|---|---|---|---|---|
| Monamate LNT-40 | 2.0 | 3.0 | 4.0 | 5.0 |
| Tween 20 | 2.0 | 3.0 | 4.0 | 5.0 |
| Polyacrylic acid sodium salt (40%) | 0.7 | 1.2 | 1.7 | 2.5 |
| Hydroxyethyl cellulose* | 0.6 | 0.5 | 0.4 | 0.3 |
| Sodium borate | 0.15 | 0.15 | 0.15 | 0.15 |
| Boric acid | 0.15 | 0.15 | 0.15 | 0.15 |
| Bronopol** | 0.1 | 0.1 | 0.1 | 0.1 |
| EDTA | 0.06 | 0.06 | 0.06 | 0.06 |
| Deionized water (qs to) | 100 | 100 | 100 | 100 |
| *Natrosol 250MP | | | | |
| **Inolex Chem Co. | | | | |
| pH | 6.9 | 6.8 | 6.7 | 6.7 |
| Viscosity (cps) | 93 | 65 | 39 | 24 |
| Appearance | clear | clear | clear | clear |

EXAMPLE 3

The following soft contact lens cleaning formulations (in weight %) illustrate the use of carboxymethyl cellulose as the anti soil redeposition agent.

| | A | B | C |
|---|---|---|---|
| Monateric LM-M30 | 0.1 | 0.2 | 0.3 |
| Pluronic F127 | 1.0 | 1.5 | 2.0 |
| Carboxymethyl cellulose* | 1.0 | 1.0 | 1.0 |
| Sodium borate | 0.1 | 0.1 | 0.1 |
| Boric acid | 0.15 | 0.15 | 0.15 |
| Methyl paraben | 0.1 | 0.1 | 0.1 |
| EDTA | 0.05 | 0.05 | 0.05 |
| Deionized water (qs to) | 100 | 100 | 100 |
| *Hercules CMC 7LF | | | |
| pH | 8.0 | 8.0 | 8.1 |
| Viscosity (cps) | 9 | 10 | 11 |
| Appearance | clear | clear | clear |

EXAMPLE 4

The following rigid contact lens cleaning formulations (in weight %) illustrate the use of poly(acrylic acid-co-maleic acid), sodium salt MW 50,000, as the anti soil redeposition agent.

| | A | B | C |
|---|---|---|---|
| Phosphoteric TC-6 | 1.0 | 2.0 | 3.0 |
| Triton X-100 | 0.5 | 0.6 | 0.7 |
| poly(acrylic acid-co-maleic acid), sodium salt | 0.2 | 0.2 | 0.2 |
| Phosphoric acid, dibasic | 0.3 | 0.3 | 0.3 |
| Methyl paraben | 0.1 | 0.1 | 0.1 |
| EDTA | 0.05 | 0.05 | 0.05 |
| Deionized water (qs to) | 100 | 100 | 100 |
| pH | 7.6 | 7.5 | 7.4 |
| Viscosity (cps) | 1 | 2 | 1 |
| Appearance | clear | clear | clear |

EXAMPLE 5

The following rigid contact lens cleaning formulations (in weight %) illustrate the use of polymethacrylic acid, sodium salt, as the anti soil redeposition agent.

| | A | B | C |
|---|---|---|---|
| Rhodapex EST-30 | 1.0 | 2.0 | 3.0 |
| Triton X-100 | 0.5 | 0.7 | 1.0 |
| polymethacrylic acid, sodium salt | 1.0 | 1.0 | 1.0 |
| Sodium borate | 0.15 | 0.15 | 0.15 |
| Methyl paraben | 0.15 | 0.15 | 0.15 |
| EDTA | 0.05 | 0.05 | 0.05 |
| Deionized water (qs to) | 100 | 100 | 100 |
| pH | 8.4 | 8.5 | 8.6 |
| Viscosity (cps) | 1 | 1 | 2 |
| Appearance | clear | clear | clear |

EXAMPLE 6

The following rigid contact lens cleaning formulations (in weight %) illustrate the use of a carboxymethyl cellulose as the anti soil redeposition agent.

| | A | B | C | D |
|---|---|---|---|---|
| Monateric CAB-LC | 0.5 | 1.0 | 2.0 | 3.0 |
| Triton X-100 | 0.1 | 0.3 | 0.5 | 0.7 |
| Polyacrylic acid sodium salt (40%) | 0.7 | 1.2 | 1.7 | 2.5 |
| Carboxymethyl cellulose* | 0.5 | 1.0 | 1.5 | 2.0 |
| Sodium borate | 0.15 | 0.15 | 0.15 | 0.15 |
| Boric acid | 0.4 | 0.4 | 0.4 | 0.4 |
| Methyl paraben | 0.15 | 0.15 | 0.15 | 0.15 |
| EDTA | 0.05 | 0.05 | 0.05 | 0.05 |
| Deionized water (qs to) | 100 | 100 | 100 | 100 |
| *Hercules CMC 7MF | | | | |
| pH | 7.8 | 7.7 | 7.6 | 7.6 |
| Viscosity (cps) | 12 | 43 | 125 | 300 |
| Appearance | clear | clear | clear | clear |

EXAMPLE 7

An example of a preferred formulation for the daily cleaning of RGP contact lenses is provided with the preferred manufacturing process and final physical properties.

| Constituent | % by weight |
|---|---|
| Amphoteric surfactant | 0.1 to 2.0 |
| Non-ionic surfactant | 0.1 to 2.0 |
| Anionic polymer, sodium salt | 0.5 to 5.0 |
| Buffering agent | 0.2 to 1.5 |
| Antimicrobial agent | 0.1 to 0.3 |
| Sequestering agent | 0.01 to 0.15 |
| Hydrochloric acid, 1N | as required to adjust pH |
| Sodium hydroxide, 1N | as required to adjust pH |
| Purified water | balance to 100 |

The formulations of Example 7 are prepared by placing approximately 75% of the total water anticipated into a suitable vessel. With stirring, add the buffering agent the sequestering agent, the antimicrobial agent and the anionic polymer, sodium salt. Heat the water to about 40–60 C to dissolve all ingredients completely. Discontinue heating and add the amphoteric and the non-ionic surfactant. Mix for about 30 minutes, then add the rest of the water to bring the formulation to 100%. Mix an additional 30 minutes. Filter batch through a 70 micron filter and sterilize at 121 C for 40 to 50 minutes. Fill bottles in a class 100 clean room.

The resulting cleaning formulations will have a pH range of 6.0 to 8.5 and a viscosity of 50 to 200 cps.

EXAMPLE 8

An example of a more preferred formulation for the daily cleaning of RGP contact lenses is provided with the preferred manufacturing process and final physical properties.

| Constituent | % by weight |
|---|---|
| Alkylamindopropyl betaines | 0.1 to 2.0 |
| Polyoxyethylene alkylphenyl ethers | 0.1 to 2.0 |
| Carboxymethylcellulose, sodium salt | 0.5 to 5.0 |
| Boric acid/soidum borate | 0.2 to 1.5 |
| alkyl paraben | 0.1 to 0.3 |
| Edetate disodium | 0.01 to 0.15 |
| Hydrochloric acid, 1N | as required to adjust pH |
| Sodium hydroxide, 1N | as required to adjust pH |
| Purified water | balance to 100 |

The formulations are prepared by the procedure following Example 7. The resulting cleaning formulations have a pH range of 7.0–8.0 and a viscosity of 80 to 150 cps.

EXAMPLE 9

An example of a most preferred formulation for the daily cleaning of RGP contact lenses is provided with the preferred manufacturing process and final physical properties.

| Constituent | % by weight |
|---|---|
| Cocoamindopropyl betaine | 0.5 to 1.0 |
| Polyoxyethylene(10) isooctylphenyl ether | 0.3 to 0.7 |
| Carboxymethylcellulose, sodium salt | 0.5 to 2.0 |
| Boric acid | 0.3 to 0.5 |
| Sodium borate | 0.05 to 0.15 |
| Methyl paraben | 0.10 to 0.20 |
| Edetate disodium | 0.03 to 0.07 |

-continued

| Constituent | % by weight |
|---|---|
| Hydrochloric acid, 1N | as required to adjust pH |
| Sodium hydroxide, 1N | as required to adjust pH |
| Purified water | balance to 100 |

The formulations are prepared by the procedure given following Example 7. The resulting cleaning formulations have a pH range of 7.0 to 8.0 and a viscosity of 80 to 150 cps.

EXAMPLE 10

To further illustrate the utility of the present invention, cleaning solutions in accordance with the formulations given in Example 9 were provided to several adapted rigid gas permeable (RGP) contact lens wearers to evaluate. These subjects replaced their normal cleaning solutions with the solutions of this invention and were told to resume their usual cleaning and care regimen. The cleaning method of the regimen is conventional, and starts with placing a worn (soiled) RGP lens in the palm of the hand, and adding a drop or two of the cleaner. The soiled lens is then digitally rubbed with the cleaner for 10 to 20 seconds. The lens is then rinsed with tap water for 5 to 10 seconds and placed in a wetting, soaking and disinfecting solution for several hours before wear. The cleaning formulations of Example 9 were found to clean soils from the worn lens surface very quickly and thoroughly. In addition, the cleaning formulation rinsed from the lens surface in seconds and did not leave cleaner residue on the lens surface. The subjects evaluating the cleaning formulation of Example 9 found them to be superior to the cleaning products they were currently using.

It will be understood that a person skilled in the art may make modifications to the preferred embodiment shown herein within the scope and intent of the claims. While the present invention has been described and carried out in a specific embodiment thereof, it is not intended to be limited thereby but is intended to cover the invention broadly within the scope and spirit of the claims.

What is claimed is:

1. An aqueous contact lens cleaning composition comprising:

a water soluble polymer having a molecular weight greater than 1000 daltons and including a plurality of carboxylate groups in one of an acid form and a salt form;

an amphoteric surfactant;

a non-ionic surfactant;

a buffering agent;

an anti-microbial agent;

water; and wherein the cleaning composition has a pH of from about 6 to about 8 and a viscosity from about 10 to about 200 cps, wherein:

the water soluble polymer is one of carboxymethyl cellulose and polyacrylic acid;

the amphoteric surfactant is cocoamidopropyl betaine;

the non-ionic surfactant is polyoxyethylene (10) isooctylphenyl ether;

the buffering agent is a mixture of boric acid and sodium borate; and the anti-microbial agent is a mixture of methylparaben and disodium edetate.

2. The cleaning composition of claim 1, wherein:

the carboxylmethyl cellulose is present in an amount of 0.5 to 5.0 weight percent;

the cocoamidopropyl betaine is present in an amount of 0.1 to 2.0 weight percent;

the polyoxyethylene (10) isooctanphenyl ether is present in an amount of 0.1 to 2.0 weight percent;

the boric acid/sodium borate buffer is present in an amount of 0.2 to 1.5 weight percent;

the methylparaben is present in an amount of 0.1 to 0.3 weight percent and the disodium edetate is present in an amount of 0.01 to 0.15 weight percent; and water is present in an amount of 89.05 to 98.99 weight percent.

3. The cleaning composition of claim 1, further including:

a viscosity building agent.

4. The cleaning composition of claim 1, wherein the composition is free of abrasive particles.

5. A method of actively preventing the redeposition of deposits and debris during a contact lens cleaning operation, the method comprising:

applying an anti-redeposition/cleaning composition to the lens, the composition including:

a water soluble polymer having a molecular weight greater than 1000 daltons and including a plurality of carboxylate groups in one of an acid form and a salt form;

an amphoteric surfactant;

a non-ionic surfactant;

a buffering agent;

an anti-microbial agent;

water; and wherein the cleaning composition has a pH of from about 6 to about 8 and a viscosity from about 10 to about 200 cps;

rubbing the cleaning composition over a surface of the lens to reduce deposits and debris present on the surface of the lens, the water soluble polymer acting as a anti-redeposition agent to prevent redeposition of deposits and debris on the lens; and rinsing the lens to remove solubilized soils and remaining cleaning composition from the surface of the lens; and wherein:

the water soluble polymer is one of carboxymethyl cellulose and polyacrylic acid;

the amphoteric surfactant is cocoamidopropyl betaine;

the non-ionic surfactant is polyoxyethylene (10) isooctylphenyl ether;

the buffering agent is a mixture of boric acid and sodium borate; and the anti-microbial agent is a mixture of methylparaben and disodium edetate.

6. The method of claim 5, wherein:

the carboxylmethyl cellulose is present in an amount of 0.5 to 5.0 weight percent;

the cocoamidopropyl betaine is present in an amount of 0.1 to 2.0 weight percent;

the polyoxyethylene (10) isooctanphenyl ether is present in an amount of 0.1 to 2.0 weight percent;

the boric acid/sodium borate buffer is present in an amount of 0.2 to 1.5 weight percent;

the methylparaben is present in an amount of 0.1 to 0.3 weight percent and the disodium edetate is present in an amount of 0.01 to 0.15 weight percent; and water is present in an amount of 89.05 to 98.99 weight percent.

7. The method of claim 5, wherein the composition is free of abrasive particles.

8. A method of passively preventing the redeposition of deposits and debris while cleaning a surface of a contact lens, the method comprising:

placing the contact lens in an anti-redeposition/cleaning composition including:

a water soluble polymer having a molecular weight greater than 1000 daltons and including a plurality of carboxylate groups in one of an acid form and a salt form;

an amphoteric surfactant;

a non-ionic surfactant;

a buffering agent;

an anti-microbial agent; and water; wherein the cleaning composition has a pH of from about 6 to about 8 and a viscosity from about 10 to about 200 cps;

allowing a predetermined time for the passive removal of deposits and debris present on the lens;

removing the lens from the cleaning composition; and wherein:

the water soluble polymer is one of carboxymethyl cellulose and polyacrylic acid;

the amphoteric surfactant is cocoamidopropyl betaine;

the non-ionic surfactant is polyoxyethylene (10) isooctylphenyl ether;

the buffering agent is a mixture of boric acid and sodium borate; and the anti-microbial agent is a mixture of methylparaben and disodium edetate.

9. The method of claim 8, further including:

rinsing the contact lens with a solution subsequent to removing the contact lens from the cleaning composition.

10. The method of claim 8, wherein:

the carboxylmethyl cellulose is present in an amount of 0.5 to 5.0 weight percent;

the cocoamidopropyl betaine is present in an amount of 0.1 to 2.0 weight percent;

the polyoxyethylene (10) isooctanphenyl ether is present in an amount of 0.1 to 2.0 weight percent;

the boric acid/sodium borate buffer is present in an amount of 0.2 to 1.5 weight percent;

the methylparaben is present in an amount of 0.1 to 0.3 weight percent and the disodium edetate is present in an amount of 0.01 to 0.15 weight percent; and water is present in an amount of 89.05 to 98.99 weight percent.

11. A method of suspending deposits and debris contained on a surface of a contact lens, the method comprising:

applying an anti-redepositional cleaning agent to the lens, the agent including:

a water soluble polymer having a molecular weight greater than 1000 daltons and including a plurality of carboxylate groups in one of an acid form and a salt form;

an amphoteric surfactant;

a non-ionic surfactant;

a buffering agent;

an anti-microbial agent; and water; wherein the cleaning composition has a pH of from about 6 to about 8 and a viscosity from about 10 to about 200 cps;

rubbing the agent over a surface of the lens to reduce deposits and debris present on the surface of the lens by solubilizing the deposits and debris with the amphoteric and non-ionic surfactants;

preventing the redeposition of the solubilized deposits and debris using the water soluble polymer as an inhibitor to the deposition of the solubilized deposits and debris on the surface of the lens;

rinsing the lens to remove solubilized deposits and debris and remaining agent from the surface of the lens; and wherein:

the water soluble polymer is one of carboxymethyl cellulose and polyacrylic acid;

the amphoteric surfactant is cocoamidopropyl betaine;

the non-ionic surfactant is polyoxyethylene (10) isooctylphenyl ether;

the buffering agent is a mixture of boric acid and sodium borate; and the anti-microbial agent is a mixture of methylparaben and disodium edetate.

12. The method of claim 11, wherein:

the carboxylmethyl cellulose is present in an amount of 0.5 to 5.0 weight percent;

the cocoamidopropyl betaine is present in an amount of 0.1 to 2.0 weight percent;

the polyoxyethylene (10) isooctanphenyl ether is present in an amount of 0.1 to 2.0 weight percent;

the boric acid/sodium borate buffer is present in an amount of 0.2 to 1.5 weight percent;

the methylparaben is present in an amount of 0.1 to 0.3 weight percent and the disodium edetate is present in an amount of 0.01 to 0.15 weight percent; and water is present in an amount of 89.05 to 98.99 weight percent.

* * * * *